United States Patent [19]
Malone

[11] Patent Number: 6,014,346
[45] Date of Patent: Jan. 11, 2000

[54] MEDICAL TIMER/MONITOR AND METHOD OF MONITORING PATIENT STATUS

[75] Inventor: Kevin R. Malone, Spokane, Wash.

[73] Assignee: Accucure, L.L.C., Spokane, Wash.

[21] Appl. No.: 09/022,954

[22] Filed: Feb. 12, 1998

[51] Int. Cl.[7] .............................. G04B 47/00; G04F 8/00; G08B 23/00; A61B 5/205

[52] U.S. Cl. ........................... 368/10; 368/108; 340/573; 340/666; 600/595

[58] Field of Search .............................. 368/10, 107–113; 128/900–905; 600/595; 340/573, 666

[56] References Cited

U.S. PATENT DOCUMENTS

| | | | |
|---|---|---|---|
| 4,196,425 | 4/1980 | Williams, Jr. et al. | 340/573 |
| 4,554,930 | 11/1985 | Kress | 128/774 |
| 4,803,625 | 2/1989 | Fu et al. | 364/413.03 |
| 5,331,549 | 7/1994 | Crawford, Jr. | 364/413.02 |
| 5,375,604 | 12/1994 | Kelly et al. | 128/671 |
| 5,441,047 | 8/1995 | David et al. | 128/670 |
| 5,482,050 | 1/1996 | Smokoff et al. | 128/710 |
| 5,534,851 | 7/1996 | Russek | 340/573 |
| 5,544,649 | 8/1996 | David et al. | 128/630 |
| 5,555,224 | 9/1996 | DePonty et al. | 368/10 |
| 5,558,638 | 9/1996 | Evers et al. | 604/66 |
| 5,583,832 | 12/1996 | DePonty | 368/10 |
| 5,844,488 | 12/1996 | Musiak | 540/573 |

*Primary Examiner*—Vit Miska
*Attorney, Agent, or Firm*—Wells, St. John, Roberts, Gregory & Matkin, P.S.

[57] ABSTRACT

A portable electronic device is disclosed for timing and monitoring patient sedentary inactivity. The device includes circuitry, a timer, an output device, and a patient reposition sensor. The timer is coupled with the circuitry and operative to measure an interval of time having a selected duration representative of sedentary positioning of a patient. The output device is coupled to the circuitry and operative to notify a health care provider of the need to perform a medical treatment upon completion of measurement of the interval of time. The patient position sensor is configured to detect a sedentary patient condition. The circuitry is operative to reinitialize the timer to begin timing the selected duration upon the sensor detecting interruption of the sedentary patient condition. Alternatively, a tactile input device can be provided to enable a caregiver to manually input the beginning of patient sedentary inactivity following repositioning of a patient. Further alternatively, output devices can comprise a nurse call station, a remotely positioned light, a light-emitting diode, a speaker or a documentation system. A method is also disclosed for implementing timing and monitoring of patient sedentary inactivity to determine repositioning requirements.

31 Claims, 7 Drawing Sheets

MEDICAL TIMER/MONITOR AND METHOD OF MONITORING PATIENT STATUS

TECHNICAL FIELD

This invention relates to apparatus and methods for monitoring patient status, and more particularly to apparatus and methods for monitoring and timing periods of patient inactivity and communicating monitored patient activity to a health care provider to direct a responsive, healthful remedial action based upon monitored and timed patient activity/inactivity.

BACKGROUND OF THE INVENTION

The management of medical treatments for inactive, bedridden and/or sedentary patients has been widely proposed and is well understood in the art. In general, the monitoring of patient sedentary positioning has been a time-consuming and laborious process requiring the efforts of a skilled or semi-skilled health care provider. The advent of managed health care and the implementation of health care services by a staff overseeing a large number of patients has complicated such efforts in that many patients require monitoring by a handful of health care personnel. Furthermore, shift changes between health care personnel can make it difficult to provide care when needed as each shift places a new health care worker in a situation where previous medical treatment is not intimately known. Such lack of histological data often leads to inaccurate delivery of timed treatments since the new health care worker may misjudge the timing of health care delivery.

One medical treatment requiring timed and monitored implementation is the repositioning of patients who are substantially confined to a bed or wheelchair. Such patients have an increased risk of contracting several harmful conditions as a result of sedentary positioning for extended periods of time. One such condition is decubitus ulcers which can result from the degeneration of skin tissue often caused by restricted blood and/or oxygen flow to portions of the body, or from prolonged exposure to bodily fluids such as urine that irritate the skin.

The prolonged positioning of a patient that results in a person's body being placed in the same position in a bed or wheelchair for prolonged periods of time frequently leads to decubitus ulcers. Such prolonged positioning may restrict blood flow to major body parts or may apply a significant portion of a patient's body weight to a small portion of their body. If left untreated, advanced stages of decubitus ulcers can pose a significant threat to a patient from related infections from bacterial and/or viral strains. An even greater threat can be imposed from exposure to potentially life-threatening strains such as staph infections. The elderly especially face risk from such infections, particularly as a result of the existence of muscle loss stemming from the aging process.

Additionally, the ineffective or infrequent management of bodily fluids such as bodily waste can lead to periods of extended exposure which can spread bacteria and other organisms. This may also lead to irritating rashes, urinary tract infections (UTI), or yeast infections. Further damage can be caused in the form of harmful and permanent psychological conditions or disorders in persons having such ulcers. For example, such persons can suffer low self-esteem or depression.

Therefore, a number of systems have been developed to address the administering and monitoring of the delivery of patient care. Many of such systems are extremely costly and complex. Only a handful are relatively inexpensive and simple. In the age of managed health care, inexpensive, simple, and effective systems are in great need.

One such system is disclosed in U.S. Pat. No. 5,555,224, directed to a visual wheelchair seating indicator having a mechanically movable pointer configured for positioning on a graduated time scale and owned by the assignee of the present invention. However, such time monitoring device requires visual identification of the pointer as it is positioned along the time scale and does not provide for physical detection of patient repositioning. Furthermore, such system does not provide for remote alert features in the form of visual, audio and nurse call station monitoring output signals. Even furthermore, such system requires the use of a separate watch or clock which requires a user to first identify the pointer position along the time scale, then identify and compare the actual time from a separate clock in order to determine when a patient needs to be repositioned. Even furthermore, such a system is securely mounted onto a wheelchair and does not provide portable features which enable movement of the seating indicator to accompany the movements of a patient from one sedentary location to another, such as from one bed to another bed, or a chair.

Another such system is disclosed in U.S. Pat. No. 5,583,832, directed to a medical timing device and owned by the assignee of the present invention. However, such system only provides for an audible sound such as an audible alarm sound comprised substantially of a single frequency, and does not provide for visual, audible, and/or nurse call station messaging, particularly remote from a patient location. Even further, such system does not provide for detection of patient repositioning.

Therefore, there is a need to provide a portable, lightweight, and low-cost medical timer/monitor for monitoring patient status. Furthermore, there is a need to provide an apparatus for remotely alerting a caregiver when a patient needs to be repositioned. Particularly, there is a need to provide for a low cost apparatus that can be used with several input and output devices to alert a caregiver to a detected patient condition. Even furthermore, there is a need to provide for such a device in a low-cost and portable manner such that the benefits of such device can be shared by many patients, even those having less financial means. Furthermore, with increases in the rate with which home health care is being implemented, there is a need to provide for lightweight and portable features such that the movement of a patient between sedentary locations, such as chairs, couches, beds and vehicles, enables a caretaker and/or user to transport the patient reposition monitor/reminder as a patient is transported between sedentary locations.

It is therefore a general object of the present invention to provide an apparatus of the described character that is of simple and economical construction, that is remotely transportable and operable via battery power and/or external power, that does not obstruct daily activity, in which the apparatus/monitor employed by the patient or other monitoring person is transportable in the hand, pocket or on the person, or in association with the person for monitoring the sedentary inactivity of a patient during an extended period of sitting or lying down, and that indicates a desired audible and/or visual instruction in the form of a visual or audible reminder, to a caregiver at selected intervals and having a desired output.

It is an object of the present invention to provide a timing apparatus for effectively managing repositioning of a patient confined to a bed or wheelchair.

It is another object of the invention to provide an inexpensive apparatus that is easy to manufacture and cost effective to be associated with each bed in a health care facility.

Yet another object of the invention is to provide for sensing of patient repositioning operative to restart timing of patient positioning so as to enable a determination of when a patient needs further repositioning.

Yet still another object of the invention is to provide for remote notification of the need to reposition a patient to a health care giver.

It is a further object of the present invention to provide for record keeping of patient treatments such as patient repositioning undertaken by a patient health care provider.

It is therefore a general object of the present invention to provide an apparatus of the described character that is of simple and economical construction, that is remotely transportable and operable via battery power or removable AC power, that does not obstruct daily activity, in which the apparatus/monitor employed by the patient or other monitoring person is transportable between a number of bed or seating positions in the hand or pocket for monitoring the sedentary inactivity of a patient during an extended period of sitting or lying down, and that indicates a desired visual alarm to a care provider at a remote location at selected intervals and having a desired output.

BRIEF DESCRIPTION OF THE DRAWINGS

Preferred embodiments of the invention are described below with reference to the following accompanying drawings.

FIG. 4 is a drawing layout sheet illustrating the assembly of FIGS. 5A–5B for an electrical schematic diagram of a second embodiment patient medical timing/monitoring apparatus in accordance with this invention as shown in FIG. 1, and having the additional feature of a bed patient sensor for monitoring patient inactivity and for transmitting remote patient care instructions to a health care provider.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

According to one aspect of the invention, a portable electronic device is disclosed for timing and monitoring patient sedentary inactivity. The device includes circuitry, a timer, an output device, and a patient reposition sensor. The timer is coupled with the circuitry and operative to measure an interval of time having a selected duration representative of sedentary positioning of a patient. The output device is coupled to the circuitry and operative to notify a health care provider of the need to perform a medical treatment upon completion of measurement of the interval of time. The patient position sensor is configured to detect a sedentary patient condition. The circuitry is operative to reinitialize the timer to begin timing the selected duration upon the sensor detecting interruption of the sedentary patient condition.

According to another aspect of the invention, a portable electronic device is provided for timing and monitoring a patient's sedentary inactivity. The device includes a portable housing, circuitry, a timer, a switch and an output device. The circuitry is carried by the housing. The timer is carried by the housing and is coupled with the circuitry. The timer is operative to measure an interval of time having a selected duration representative of sedentary positioning of a patient. The switch is coupled with the timer and is configured to reset the timer in association with a caregiver repositioning a patient. The output device is positioned remotely of the housing and is coupled to the circuitry. The output device is operative to notify a health care provider of the need to perform a medical treatment upon completion of measurement of the interval of time. The timer is operative to remotely alert a caregiver of a need to reposition a patient.

According to yet another aspect of the invention, a method is provided for managing timed patient repositioning of a sedentary patient. A device having circuitry, an output device coupled to the circuitry, and a sensor coupled with the circuitry for detecting a patient's sedentary condition forms a medical timing and monitoring apparatus. The method includes the steps of detecting a sedentary positioning of a patient; timing an interval of time having a selected duration representative of sedentary positioning of a patient; resetting the interval of time upon detection of the patient being repositioned; and outputting a signal to a caregiver responsive to completion of the timed interval of time indicative of the need to reposition the patient.

Figure 1:
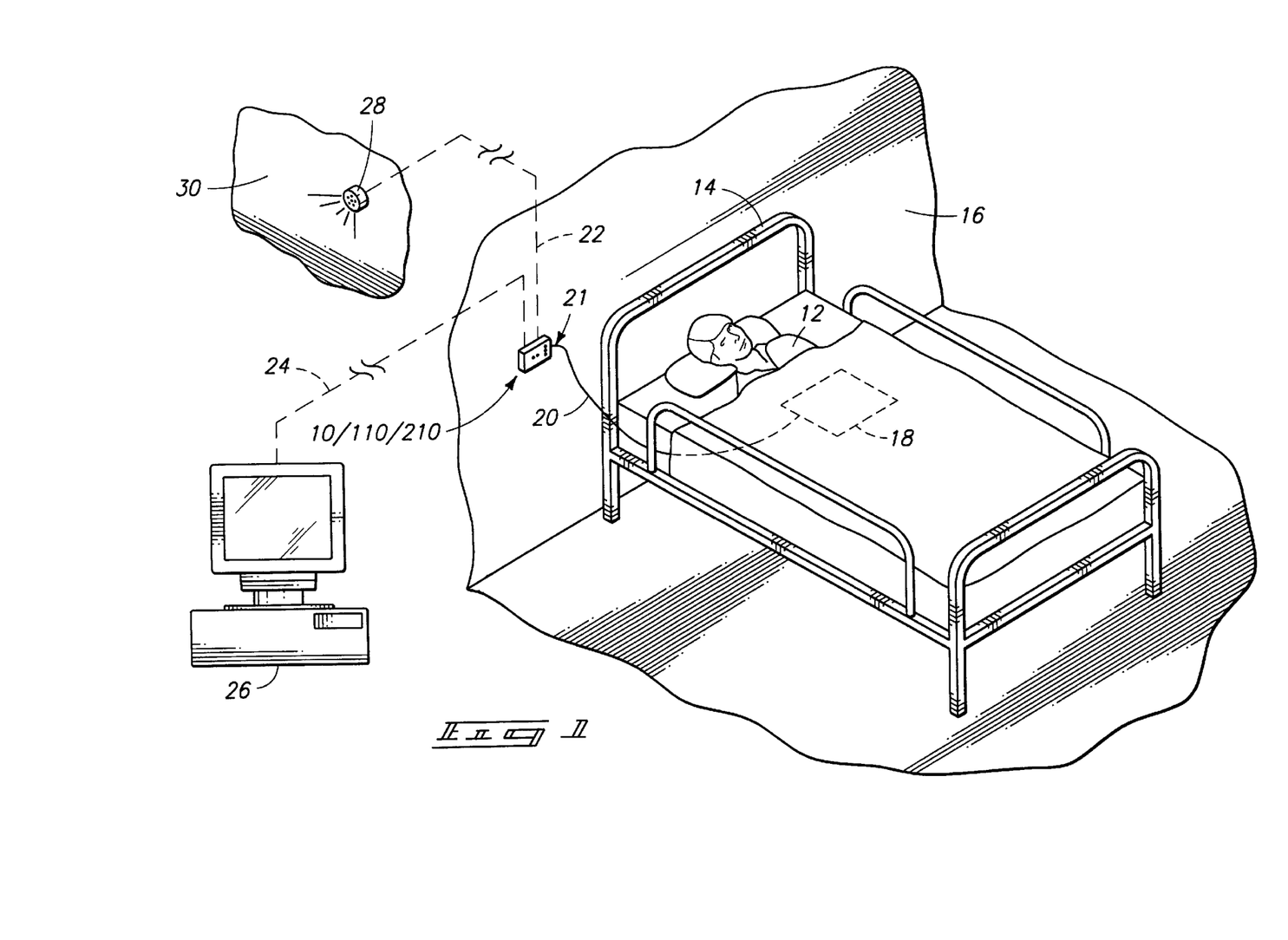
FIG. 1 is a perspective view of a portable electronic apparatus configured as a patient medical timing/monitoring apparatus that is removably mounted to a wall adjacent to a hospital bed for monitoring patient inactivity and for notifying a health care provider of monitored patient sedentary inactivity in accordance with several presently preferred implementations of the invention.

A preferred embodiment portable electronic device in accordance with the invention is first described with reference to FIGS. 1–3. Such figures show various aspects and dimensional characteristics described further below with respect to a patient medical timing and monitoring apparatus. The portable electronic device is designated in FIGS. 1–3 generally with reference numeral 10. Optional embodiments are illustrated in FIG. 1 as reference numerals 110 and 210, and are further described with reference to FIGS. 4–5 and 6, respectively. The housing, or case, depicted as apparatus 10 in FIG. 1 is understood to be representative of the housing for apparatus 110 and 210, but requiring slight modifications to the buttons and display features to enable the constructions detailed with reference to a first alternative embodiment depicted in FIGS. 4–5 and a second alternative embodiment depicted in FIG. 6.

According to a first implementation of the invention, medical timing/monitoring apparatus 10 comprises a portable patient monitor and timing system configured for removable mounting in a location in close association with a patient, or on a patient support structure, within a patient room. As shown in FIG. 1, medical timing/monitoring apparatus 10 (and alternative embodiments 110 and 210) is removably mounted adjacent to a patient support structure within a hospital room, here on a wall 16 of a patient room. One such patient support structure comprises a hospital bed 14, as shown in FIG. 1. Other patient support structures might comprise a seat, a wheelchair, or some other patient support structure. Optionally, such device can be hand-held or user worn.

One technique for removably mounting apparatus 10 to a wall, patient, or patient support structure is to use hook and loop-type fasteners. Such hook and loop-type fasteners are configured one to the apparatus and the other to the patient support structure to removably secure apparatus 10 to such a support structure. Other techniques include the use of one or more fasteners such as threaded fasteners, rivets, bolts, clips, and/or magnetized components configured to secure apparatus 10 to a support structure.

As shown in FIG. 1, medical timing/monitoring apparatus 10 is shown mounted to a wall 16 of a patient's room. Medical timing/monitoring apparatus 10 is provided in close association with patient 12 in order to facilitate easy finger manipulation of apparatus 10 to record patient repositioning by a caregiver immediately following repositioning of the patient 12. Optionally, medical timing/monitoring apparatus 10 can be mounted to bed 14 or a chair, such as a wheelchair. Timing/monitoring apparatus 10 is positioned within arms-reach of a caregiver and/or a patient to facilitate reconfiguring of one or more switches on apparatus 10 which indicate repositioning of a patient by a caregiver. According to the one construction, timing/monitoring apparatus 10 is configured to be quickly and easily removably received on a support structure such as wall 16. Optionally, such apparatus 10 can be permanently secured to a support structure.

As shown in FIG. 1, medical timing/monitoring apparatus 10 according to one implementation is signal coupled via communication lines 22 and 24 with a nurse call station 26 and a hallway light 28, respectively. According to other implementations, medical timing/monitoring apparatus 110 and 210 are each further coupled via signal cable 20 with a patient pressure sensor 18. Nurse call station 26 and hallway light 28 each comprise an output device that is coupled with medical timing/monitoring apparatus 10 at a location remote from a patient 12. Such apparatus 10 is operative to notify caretakers of a need to reposition the patient so as to prevent bedsores, ulcers, and/or other skin conditions associated with prolonged sedentary positioning of a patient.

Patient position sensor 18 comprises a commercially available bed switch such as a membrane switch formed from conductive silver ink. Such a position sensor 18 forms a pressure sensitive switch operative to detect presence of a sedentary patient atop the switch for a continuous, uninterrupted period of time. Optionally, sensor 18 comprises a capacitive grid sensor operative to detect capacitive changes imparted from proximate positioning of a patient immediately adjacent the sensor. Sensor 18 is operatively signal coupled with medical timing/monitoring apparatus 110 and 210 to detect movement of patient 12 such that a timer, comprising a clock, of apparatus 110 and 210 is reset if sensor 18 is unloaded. Cable 20 signal couples sensor 18 with medical timing/monitoring apparatus 110 and 210 via a cable connector 21.

Nurse call station 26 comprises a central work area within a hospital, typically associated with a medical ward and a group of rooms containing medical patients, where the administration of health care is managed. More particularly, a nurse call station can include a work area containing equipment for managing paperwork, patient charting, writing up orders, etc., and typically includes a monitor board having lights and/or speakers for alerting an attending nurse of the triggering of a patient alarm. One such alarm comprises a nurse call button placed on a patient bed which enables a patient to alert a nurse when, for example, an IV is blocking up on the patient. Other such alarms comprise a computer monitor configured to visually alert a nurse to the status of monitored patient conditions and/or the alerting by a patient of a patient condition. For purposes of simplification, a nurse call station is illustrated in FIG. 1 in the form of a computer monitor capable of visually/audibly alerting a caregiver of patient status.

Hallway light 28 comprises an optical output device mounted to a hallway wall 30 within a hospital, or in a room, where caregivers can be visually alerted to patient conditions such as positioning status. One such room is a patient room having an attending nurse. Another such room is a central nurse station where an attending nurse can visually identify operation of light 28 responsive to a detected need to reposition, or turn, a sedentary patient. Light 28 can be formed from any light capable of visually alerting a caregiver including incandescent, fluorescent, flashing or other visible electromagnetic radiation.

Figure 2:
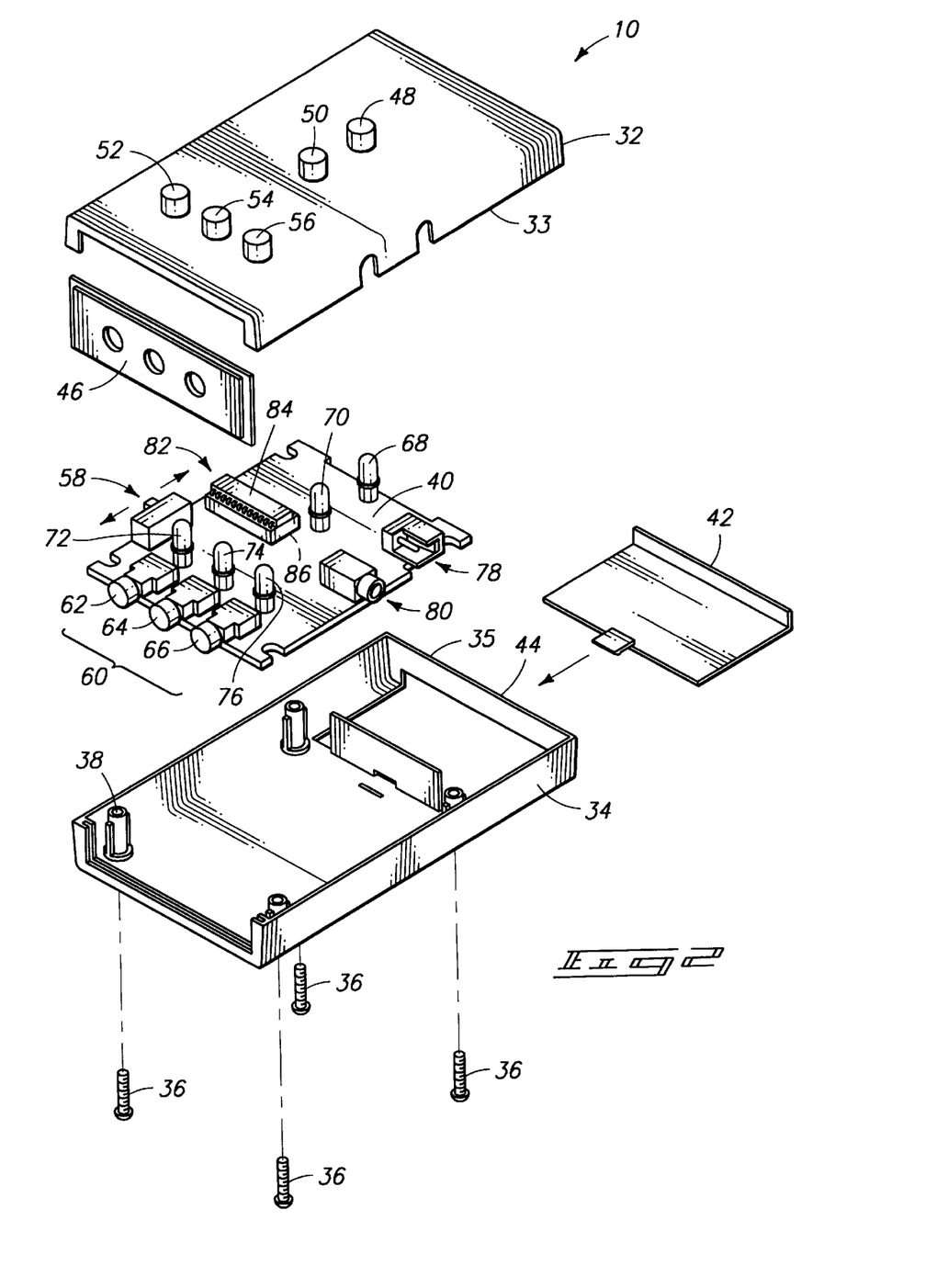
FIG. 2 is an enlarged, exploded perspective view of one implementation of the patient medical timing/monitoring apparatus depicted in use in FIG. 1 and illustrating internal operating components.

FIG. 2 illustrates medical timing/monitoring apparatus 10 in an exploded perspective view, illustrating the construction, assembly and packaging features provided for associated mechanical, electrical and electronic components. More particularly, a front housing shell 32 and a rear housing shell 34 are removably secured together with a plurality of threaded fasteners 36. Each fastener 36 is received through an aperture boss 38 in shell 34 and into a threaded boss (not shown) of shell 32. Hence, shells 32 and 34 are secured along a pair of associated mating edges 33 and 35, respectively. Shells 32 and 34 cooperate with an end plate 46 to form a housing for internally supporting associated mechanical and electrical/electronic components of timing/monitoring apparatus 10. To facilitate quick and easy hand mounting/demounting from wall 16, hook and loop fasteners are used to secure apparatus 10 to the back, outer surface of shell 34.

Shells 32 and 34 cooperate with end plate 42 to support and house output devices and interface devices. Such output and interface devices are provided in association with a printed circuit (PC) board 44, and are configured to enable detection of patient repositioning and report the need to reposition a patient to a caregiver. More particularly, shells 32, 34 and end plate 42 cooperate in assembly to provide a housing for supporting and encasing printed circuit (PC) board 44 and a portable power supply such as a battery (not shown). Although not depicted in the FIG. 2 configuration, batteries can be optionally provided for powering apparatus 10, within a battery tray 40, beneath a battery cover 42. Cover 42 is removably fitted to shell 34 to encase batteries (not shown) within the corresponding housing, and is configured to form a substantially flush, conforming outer surface with the outer surface of shell 22.

Figure 3:
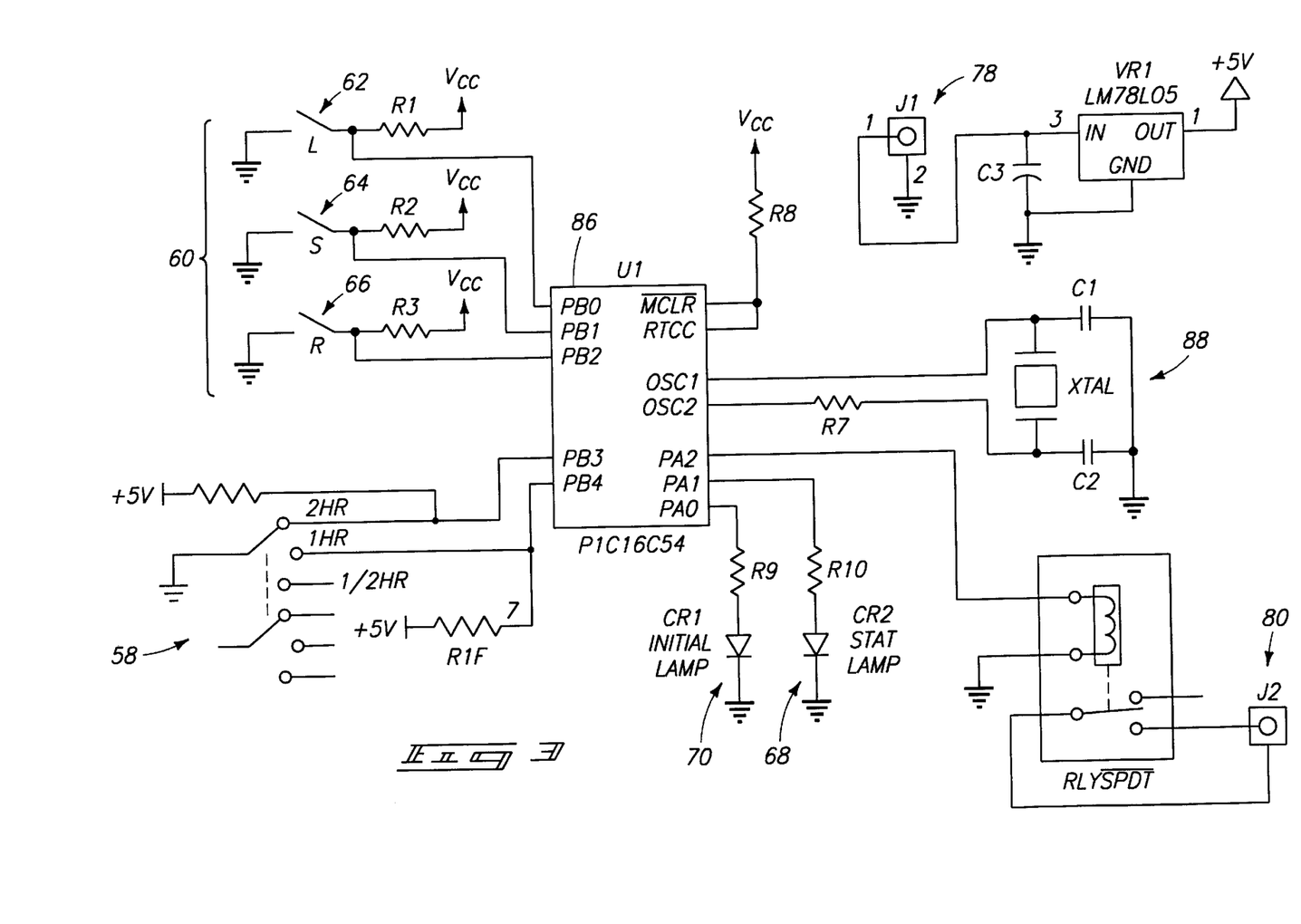
FIG. 3 is a fragmentary electrical schematic diagram showing the patient medical timing/monitoring apparatus of FIG. 2 in greater detail.

As shown in FIG. 2, printed circuit (PC) board 44 contains electric/electronic circuitry configured to implement the circuitry depicted with reference to FIG. 3. A similar printed circuit board and housing are used to house and implement the alternative embodiments comprising the circuit diagrams of FIGS. 4–5 and 6, respectively. More particularly, printed circuit (PC) board 44 includes an L-Pack processor and memory chip component 82 (U1) comprising an EPROM 84, a Digital Signal Processing (DSP) chip comprising a processor 86, and additional operating circuitry. Further details of such operating circuitry are described below with reference to FIG. 3.

EPROM 40 comprises one form of a record storage system suitable for storing and retrieving information from input devices and for directing output devices associated with timing/monitoring apparatus 10. EPROM 40 can be used to store algorithms used in implementing notification of caregivers via output devices responsive to detection of patient sedentary conditions from input devices.

As shown in FIG. 2, output devices include a plurality of light emitting diodes 68, 70, 72, 74 and 76. Each of diodes 68, 70, 72, 74 and 76 is operatively carried by printed circuity (PC) board 44 between shells 32 and 34. PC board 44 is carried in nested engagement between the outer bodies formed from aperture bosses 38 such that each of diodes 68, 70, 72, 74 and 76 extends within an optically transparent lenses 48, 50, 52, 54 and 56, respectively, that are mounted within apertures of front shell 32. Diode 68 cooperates with lens 48 to form an optical output apparatus operative to visually alert a caregiver when a "STAT" condition exists requiring that a caregiver check the condition of a patient to determine whether repositioning is required. Diode 70 cooperates with lens 50 to form an optical output apparatus operative to visually alert a caregiver when an "ALERT" condition exists requiring that a caregiver immediately check the condition of a patient to reposition the patient. Diodes 72, 74 and 76 cooperate with lenses 52, 54 and 56 to form three optical output apparatus operative to visually alert a caregiver of orientation of a patient comprising a "Left Position", "Supine Position", and "Right Position", respectively.

According to one construction, diodes 68, 70, 72, 74 and 76 each emit white light. According to another construction, each of diodes 68, 70, 72, 74 and 76 emits a different, distinct color of light so as to enable visual identification of each distinct diode. According to yet another construction, each of diodes 68, 70, 72, 74 and 76 emits light in a flashing manner, with each diode emitting flashing light at a different, distinct frequency so as to enable visual identification of each distinct diode.

Additional output devices include a nurse call interface jack 80 that removably couples via a male connector plug (not shown) and a communication line 24 with nurse call station 26. Additionally or optionally, interface jack 80 can be coupled via a male connector plug and a communication line 22 with a hallway light 28 outside the patient room. As shown in FIG. 1, apparatus 10 is shown being concurrently used with nurse call station 26 and light 28 which is possible with such embodiment by coupling interface jack 80 with a single male connector plug having a signal splitter. According to the constructions of apparatus 110 and 210, several interface jacks similar to jack 80 are provided for signal coupling each output device.

Input devices include a three position time interval selection switch 58 having three predefined intervals of time for determining when a selected medical treatment comprising repositioning of a patient needs to be undertaken by a caregiver. More particularly, selected switch positions comprise 30-minute, one-hour and two-hour time intervals, respectively. Once one of the switch positions has been selected, its corresponding time interval is stored in memory. As shown in FIG. 2, switch 58 is located along a side of apparatus 10 for easy access thereto by a health care provider.

A timer (not shown) is also provided on PC board 44 for implementing timing of the predefined intervals between alerting a caregiver as shown in FIG. 2. One timer comprises a counter/oscillator in the form of a 14-bit binary counter and oscillator. One such device is a Motorola MC14060B, a 14-stage binary ripple counter with an on-chip oscillator buffer. The oscillator enables the design implementation of either RC or crystal oscillator circuits. A reset function is also provided to facilitate the placement of all outputs into a zero state, and to disable the oscillator. A negative transition on the clock is used to advance the counter to a next state. Positioning of a time interval selection switch 58 allows for programming a time period after which a selected medical treatment, such as the repositioning of a bed-confined patient or a treatment for incontinence, will be performed. Programming is provided by selectively positioning switch 58 to one of the three switch positions corresponding to a predefined time period.

An additional input device is a mode select patient position switch 60 comprising three separate electronic switches 62, 64 and 66 positioned along a top side of apparatus 10 for easy access by a health care provider. Switches 62, 64 and 66 according to one implementation correspond to a patient being oriented on a left side, in a supine position, and on a right side, respectively. It is possible to configure switches 62, 64 and 66 for independent activation. However, switches 62, 64 and 66 are preferably electronically or mechanically interrelated so that no two of them may be concurrently activated.

Medical timing/monitoring apparatus 10 includes diodes 72, 74 and 76 positioned in association with switches 62, 64 and 66 for visually indicating the selection of a medical treatment, comprising a plurality of light sources, each of which is arranged adjacent to or underneath a corresponding switch.

FIG. 3 illustrates an electrical schematic diagram corresponding to the embodiment depicted in FIGS. 1 and 2 as medical timing/monitoring apparatus 10. More particularly, such electrical schematic diagram comprises a circuit implemented on printed circuit (PC) board 44 (of FIG. 2). Time interval selection switch 58 enables selective switching between 30-minute, one-hour and two-hour time delay intervals for alerting a caregiver of a need to reposition a patient. Timing is implemented via clock 88 which enables processor 86 to alert a caregiver following completion of each preselected time interval. Output devices that are operatively coupled with processor 86 include lights, or lamps, comprising "STAT" diode 68, initial "ALERT" diode 70 and interface jack 80 comprising a female connector jack configured to be removably mated with a nurse call station, or optionally a remote hall light.

Mode select patient position switch 60 is formed from individual position switches 62, 64 and 66, each selectively signal-coupled with processor 86. Each switch can be selectively coupled to ground which applies Vcc across a respective resistor R1, R2 or R3 such that a distinct recognizable voltage is identified by processor 86.

Power jack 78 is configured to removably receive a +9-volt unregulated power supply via a complementary male connector (not shown). A +5-volt regulated output comprises Vcc which powers associated circuitry.

Figures 5, 5A, 5B:
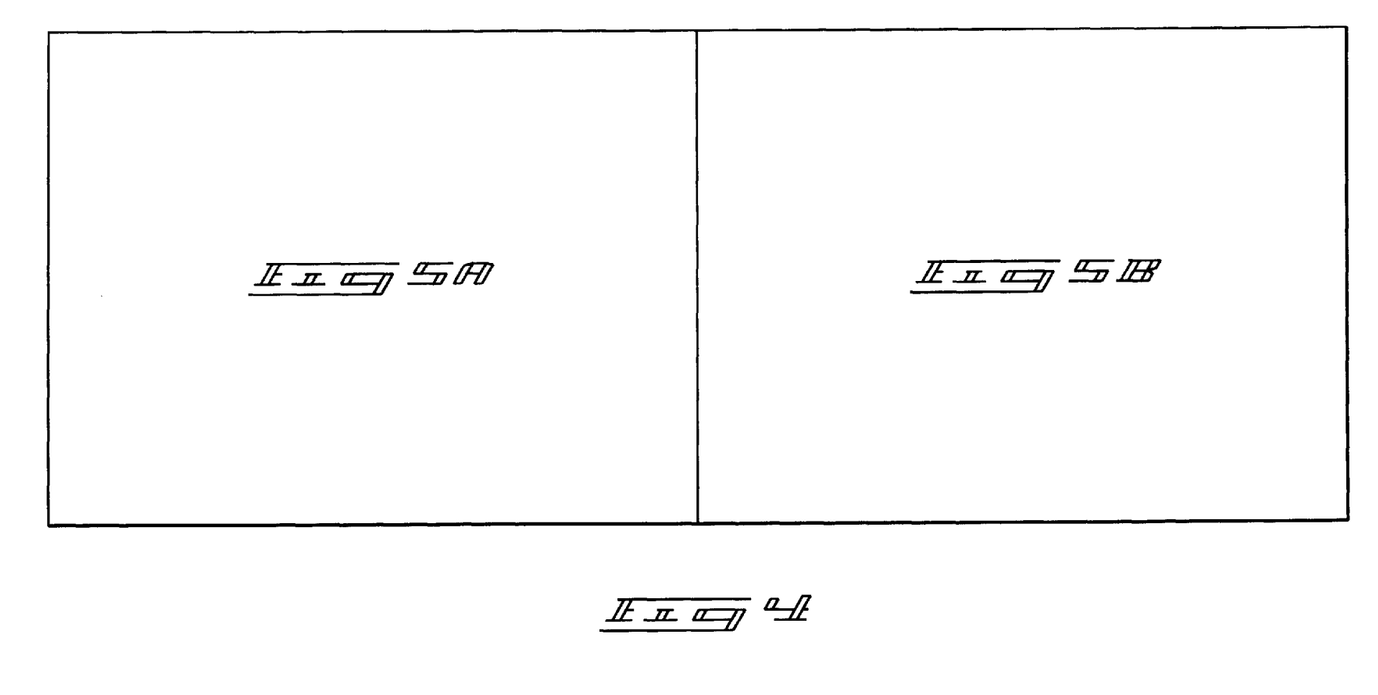
FIGS. 5A–5B illustrate an electrical schematic diagram of the patient medical timing/monitoring apparatus of FIG. 4.
Figure 5A:
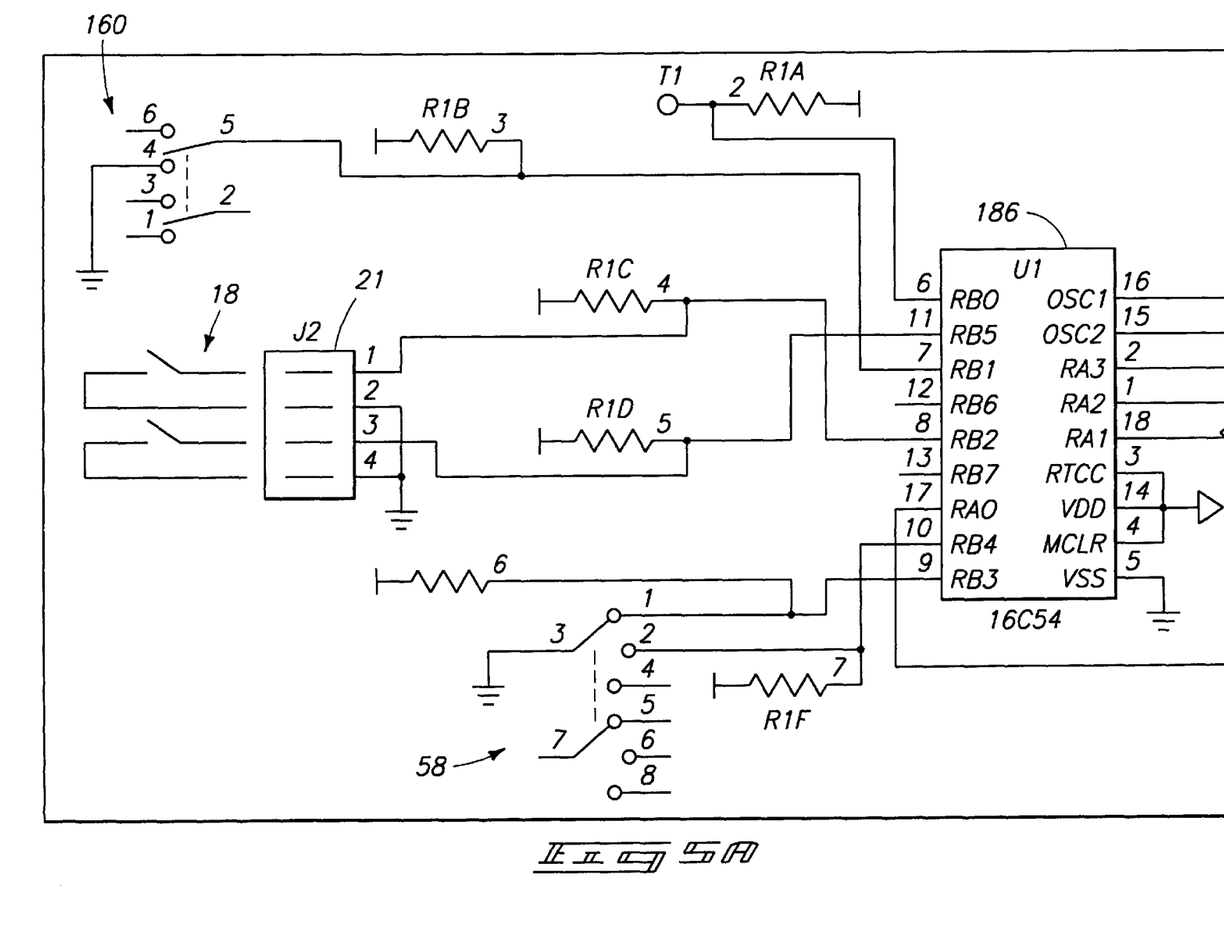
Figure 5B:
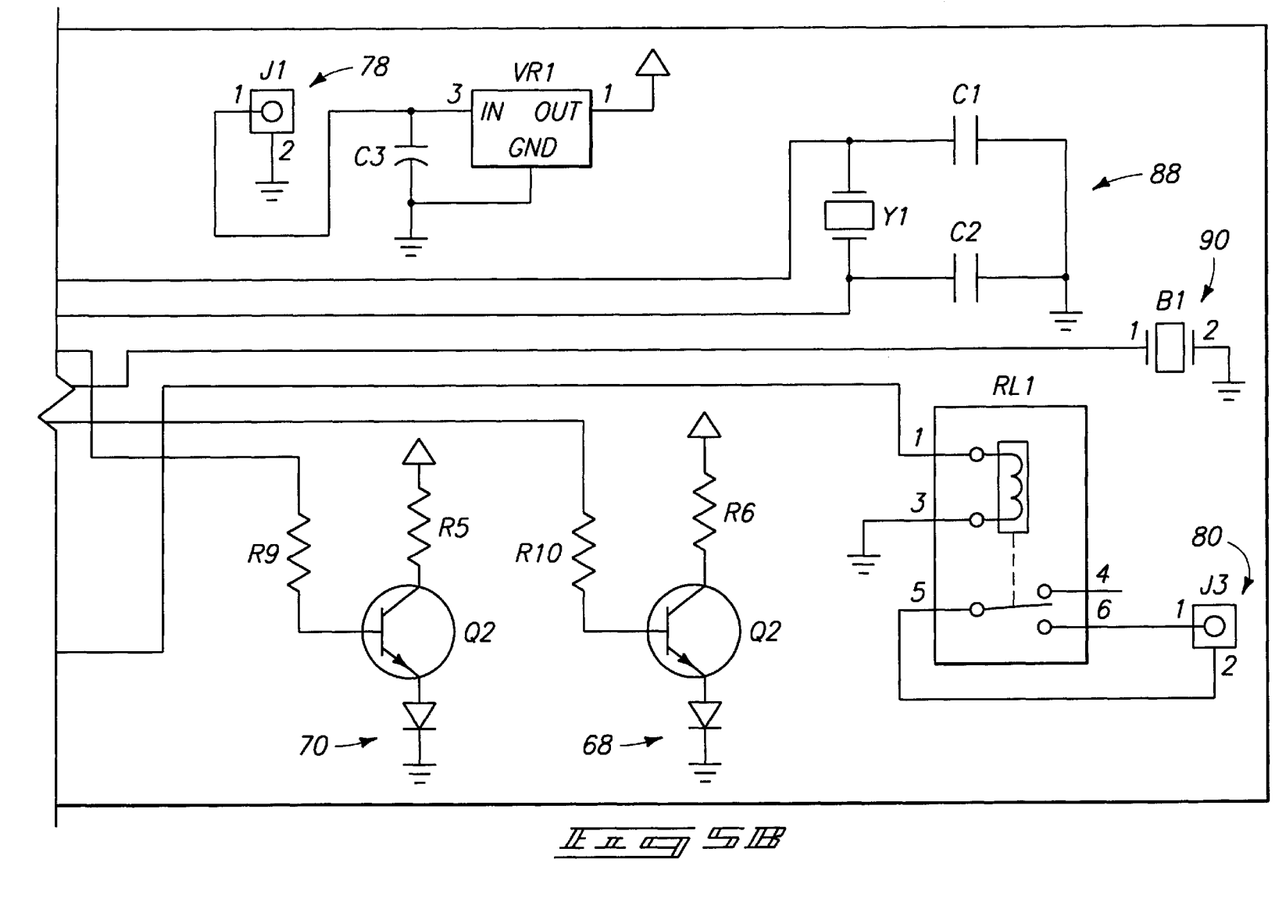

FIG. 4 shows the assembly of FIGS. 5A and 5B for illustrating an electrical schematic diagram corresponding to the alternative embodiment depicted in FIG. 1 as medical timing/monitoring apparatus 110. Such electrical schematic diagram comprises a circuit implemented on a printed circuit (PC) board similar to PC board 44 (of FIG. 2), and within a housing similar to that shown in FIG. 2.

More particularly, a mode selection switch 160 is operatively coupled with a processor 186, similar to processor 86

(of FIG. 3). Mode selection switch 160 comprises a two-way switch selectively positionable between a "reposition mode" and a "safeguard mode". The "reposition mode" operatively configures processor 186 such that the timer, comprising clock 88, is reset when a bed sensor 18 is unloaded. Such unloaded condition is indicative of a patient being repositioned by a caregiver. The "safeguard mode" operatively configures processor 186 to enable a caregiver to perform a bed check by testing bed sensor 18 so as to determine proper resetting of the timer. In such mode, an output signal is immediately generated responsive to loading/unloading of sensor 18 by a caregiver testing such sensor. One output signal is generated as a visual signal via "ALERT" diode 70. Another optional or additional output signal is generated as a visual and/or audible signal via interface jack 80 to a nurse call station 26 (see FIG. 1) or to a hallway light 28 (see FIG. 1). Yet another optional or additional output signal is generated as an audible signal via audio alarm 90, comprising a piezoelectric speaker audio output device.

According to the implementation depicted in FIGS. 1 and 5A–B and referenced as medical timing/monitoring apparatus 110, bed sensor 18 includes a signal cable that is removably coupled with apparatus 110 via a connector 21. Connector 21 is signal coupled via an interface jack, similar to jack 80 (of FIG. 2), with apparatus 110. Additionally, time interval select switch 58 is provided with a construction similar to that described in the embodiment depicted in FIG. 3. Likewise, power jack 78 is provided with a construction similar to that described in the embodiment depicted in FIG. 3. Even further, "STAT" diode 68 is provided with a construction similar to that described in the embodiment depicted in FIG. 3.

Figure 6:
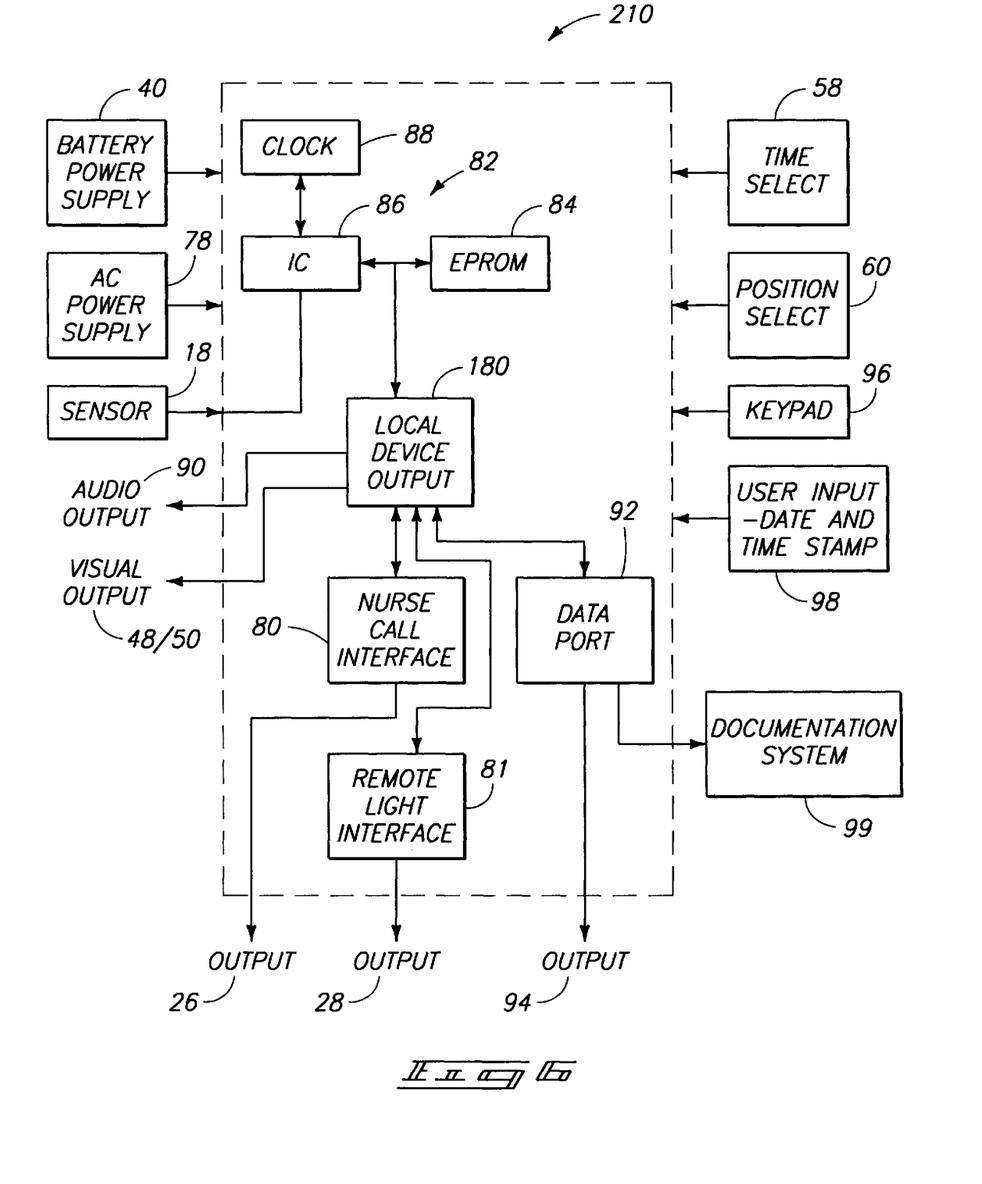
FIG. 6 is a functional block diagram of a third embodiment patient medical timing/monitoring apparatus in accordance with the present invention and including optional interface and output features.

FIG. 6 illustrates in schematic block diagram form another alternative embodiment medical timing/monitoring apparatus 210 as shown in FIG. 1. More particularly, apparatus 210 includes a number of features previously described with reference to the above-described embodiments including a battery power supply 40, an AC power supply 78, a bed patient position sensor 18, an audio output 90, visual outputs 48 and 50, time select switch 58, position select switch 60, clock 88, integrated circuit (processor) 86, EPROM 84 and L-Pack 82. However, the embodiment depicted in FIG. 6 further provides for a local device output 180, a data port 92, a data port output 94, a keypad input 96, a user input 98 and a documentation system 99. All such features are understood to be provided within a case similar to that depicted in the FIG. 2 embodiment, but with modifications suitable for accommodating such additional/modified features.

As shown in FIG. 6, a local device output 180 is configured to provide for conveying information from processor 86 to an output format suitable for output at one of several output devices. One such output device comprises audio output 90 on apparatus 210, an audio piezoelectric alarm previously described with reference to FIGS. 5A–B. Another such output device comprises one of visual outputs 48 and 50, comprising "STAT" and "ALERT" lenses and associated diodes, respectively, previously described with reference to the embodiment depicted in FIGS. 2 and 3. Yet another such output device comprises nurse call station 26 which actively couples via nurse call interface 80, as previously described in reference to FIGS. 3 and 4. It is understood that local device output 180 can comprise nurse call interface 80 in one construction.

Furthermore, yet another such output device comprises hallway light 28 which actively couples via a remote light interface 81 to visually alert a user as previously described with reference to the embodiment depicted in FIGS. 2 and 3. According to one construction, remote light interface 81 comprises an interface connector jack similar to the jack comprising nurse call interface 80 (of FIG. 2).

Even further, another output device comprises a data output 94 of a data port 92. In one version, data output 94 comprises a printhead configured to print information detailing when a patient was repositioned and the identification of the caregiver who repositioned the patient. Such data output provides a means for defending against allegations that patients have not been properly treated, or repositioned according to a defined frequency and position. Furthermore, data port 92 is configured to provide such information to a documentation system 99, preferably a central computer that tracks the frequency and type of care being administered to each patient being monitored.

One additional input device comprises a keypad 96 which enables a caregiver to enter key information relating to a patient such as care being administered, identification of the caregiver administering such case, and other vital information needed to monitor the administering of care to a patient.

Another additional input device comprises a user input 98 that enables the entering of key information relating to the administering of patient care. According to one implementation, user input 98 comprises a date and time stamp that reads a caregiver's identification via a magnetic identification card, notes the time at which care is being administered, recognizes the care being administered, and outputs a date and time to a patient chart, or to computer memory where such information can be stored for record-keeping.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A portable electronic device for timing and monitoring patient sedentary inactivity, comprising:
   circuitry;
   a timer coupled with the circuitry and operative to measure an interval of time having a selected duration representative of sedentary positioning of a patient;
   an output device coupled to the circuitry and operative to notify a health care provider of the need to perform a medical treatment upon completion of measurement of the interval of time; and
   a patient position sensor configured to detect a sedentary patient condition;
   the circuitry operative to reinitialize the timer to begin timing the selected duration upon the sensor detecting interruption of the sedentary patient condition.

2. The portable electronic device of claim 1 wherein the circuitry comprises a processor.

3. The portable electronic device of claim 1 wherein the circuitry comprises memory.

4. The portable electronic device of claim 1 wherein the timer comprises a clock.

5. The portable electronic device of claim 1 wherein the output device comprises a data port.

6. The portable electronic device of claim 1 wherein the output device comprises an audio output.

7. The portable electronic device of claim 1 wherein the output device comprises a visual output.

8. The portable electronic device of claim 1 wherein the patient reposition sensor comprises a bed switch.

9. The portable electronic device of claim 1 further comprising a time interval selection switch.

10. The portable electronic device of claim 1 further comprising a mode selection switch.

11. The portable electronic device of claim 1 further comprising an interface jack.

12. The portable electronic device of claim 1 further comprising a user input device.

13. The portable electronic device of claim 12 wherein the user input device comprises a keypad.

14. The portable electronic device of claim 12 wherein the user input device comprises an electronic switch.

15. A portable electronic device for timing and monitoring patient sedentary inactivity, comprising:

a portable housing;

circuitry carried by the housing;

a timer carried by the housing, coupled with the circuitry, and operative to measure an interval of time having a selected duration representative of sedentary positioning of a patient;

a switch coupled with the timer and configured to reset the timer in association with a caregiver repositioning a patient; and an output device positioned remotely of the housing, coupled to the circuitry, and operative to notify a health care provider of the need to perform a medical treatment upon completion of measurement of the interval of time;

the timer operative to remotely alert a caregiver of a need to reposition a patient.

16. The device of claim 15 wherein the circuitry comprises a processor.

17. The device of claim 16 wherein the portable housing comprises a front housing shell and a back housing shell.

18. The device of claim 15 wherein the timer comprises a clock.

19. The device of claim 15 wherein the switch comprises an electronic switch indicative of a patient's position.

20. The device of claim 15 wherein the output device comprises a nurse call station.

21. The device of claim 15 wherein the output device comprises a light positioned remotely of the patient and operative to alert a caregiver of a need to reposition a patient.

22. The device of claim 15 wherein the output device comprises an audio output.

23. The output device of claim 15 wherein the output device comprises a visual output.

24. The device of claim 15 further comprising a patient position sensor configured to detect a sedentary patient condition, the circuitry operative to reinitialize the timer to begin timing the selected duration upon the sensor detecting interruption of a sedentary patient condition.

25. A portable medical timing and monitoring apparatus which implements a method for managing timed patient repositioning of a sedentary patient, wherein the device includes circuitry, an output device coupled to the circuitry, and a sensor coupled with the circuitry for detecting a patient sedentary condition, the method comprising the steps of:

detecting a sedentary positioning of a patient;

timing an interval of time having a selected duration representative of sedentary positioning of a patient;

resetting the interval of time up detection of the patient being repositioned;

outputting a signal to a caregiver responsive to completion of the timed interval of time indicative of the need to reposition the patient.

26. The method of claim 25 further comprising the step of selecting an interval of time from a plurality of predefined intervals of time.

27. The method of claim 25 wherein the step of outputting a signal to a caregiver comprises visually alerting a caregiver.

28. The method of claim 25 wherein the step of outputting a signal to a caregiver comprises visually alerting a caregiver.

29. The method of claim 25 wherein the step of outputting a signal to a caregiver comprises delivering a remote signal to a nurse call station.

30. The method of claim 25 wherein the step of outputting a signal to a caregiver comprises delivering a remote signal to a hallway light.

31. The method of claim 25 further comprising the step of selecting a patient position from a plurality of patient positions indicative of a patient position requiring detection of sedentary positioning.

* * * * *

UNITED STATES PATENT AND TRADEMARK OFFICE
CERTIFICATE OF CORRECTION

PATENT NO. : 6,014,346
DATED : January 11, 2000
INVENTOR(S) : Kevin R. Malone

Page 1 of 2

It is certified that error appears in the above-identified patent and that said Letters Patent is hereby corrected as shown below:

Col. 6, line 55, delete "of shell 22", and insert --of shell 32--.

Col. 7, line 1, delete "EPROM 40", and insert --EPROM 84--.

Col. 7, line 4, delete "EPROM 40", and insert --EPROM 84--.

Col. 7, lines 14-15, delete "transparent lenses", and insert --transparent lens--.

Col. 7, line 15, delete "that are mounted", and insert --that is mounted--.

Col. 12, line 21 (claim 25), delete "up detection", and insert --upon detection--.

Col. 12, line 22 (claim 25), after "repositioned;", insert --and--.

UNITED STATES PATENT AND TRADEMARK OFFICE
CERTIFICATE OF CORRECTION

PATENT NO. : 6,014,346           Page 2 of 2
DATED       : January 11, 2000
INVENTOR(S) : Kevin R. Malone It is certified that error appears in the above-identified patent and that said Letters Patent is hereby corrected as shown below:

In the Drawings:

Figure 2, reverse reference numerals 40 and 44.

Signed and Sealed this

Twentieth Day of February, 2001

Attest:

NICHOLAS P. GODICI

Attesting Officer        Acting Director of the United States Patent and Trademark Office